United States Patent
Razavi et al.

(10) Patent No.: US 9,814,406 B2
(45) Date of Patent: Nov. 14, 2017

(54) METHOD AND SYSTEM TO IDENTIFY MOTION DATA ASSOCIATED WITH CONSISTENT ELECTRICAL AND MECHANICAL BEHAVIOR FOR A REGION OF INTEREST

(71) Applicant: PACESETTER, INC., Sunnyvale, CA (US)

(72) Inventors: Hoda Razavi, San Jose, CA (US); Fujian Qu, San Jose, CA (US); Kyungmoo Ryu, Palmdale, CA (US); Yelena Nabutovsky, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 456 days.

(21) Appl. No.: 14/478,707

(22) Filed: Sep. 5, 2014

(65) Prior Publication Data

US 2015/0141765 A1 May 21, 2015

Related U.S. Application Data

(60) Provisional application No. 61/906,305, filed on Nov. 19, 2013.

(51) Int. Cl.
*A61B 5/04* (2006.01)
*A61B 5/0468* (2006.01)
(Continued)

(52) U.S. Cl.
CPC .......... *A61B 5/0468* (2013.01); *A61B 5/1102* (2013.01); *A61B 5/721* (2013.01); *A61B 2034/2051* (2016.02)

(58) Field of Classification Search
CPC ...... A61B 5/0468; A61B 5/1102; A61B 5/721
See application file for complete search history.

(56) References Cited

U.S. PATENT DOCUMENTS 5,391,199 A 2/1995 Ben-Haim
5,713,367 A * 2/1998 Arnold ................ A61B 5/0408
600/517
(Continued)

FOREIGN PATENT DOCUMENTS

EP 1 070 480 A1 1/2001
EP 1 508 300 A1 2/2005
(Continued)

OTHER PUBLICATIONS

USPTO, "Final Office Action for U.S. Appl. No. 14/703,749", dated Jan. 23, 2017.
(Continued)

*Primary Examiner* — Christopher D Koharski
*Assistant Examiner* — Natasha Patel
(74) *Attorney, Agent, or Firm* — Theresa A. Raymer

(57) ABSTRACT

Methods and system are provided that identify motion data associated with consistent electrical and mechanical behavior for a region of interest of the heart. The methods and systems acquire electrical cardiac signals indicative of physiologic behavior of at least a portion of the heart over a plurality of cardiac cycles. The methods and systems acquires motion data indicative of mechanical behavior of a motion sensor over the plurality of cardiac cycles to form a motion data collection, the motion data indicative of mechanical behavior of the region of interest when the motion sensor is in contact with the region of interest. The designating ectopic beats within the cardiac cycles may be based on the electrical cardiac signals, the ectopic beats producing electrically inconsistent (EI) data within the motion data collection. The methods and systems identify mechanically inconsistent (MI) data within the motion data collection based on irregular changes in the motion data. The methods and systems remove at least a portion of the EI and
(Continued)

MI data from the motion data collection based on the designating and identifying operations to form an electrically/mechanically consistent (EMC) motion data collection.

20 Claims, 7 Drawing Sheets

(51) Int. Cl.
      *A61B 5/11*      (2006.01)
      *A61B 5/00*      (2006.01)
      *A61B 34/20*     (2016.01)

(56) References Cited

U.S. PATENT DOCUMENTS

| | | | |
|---|---|---|---|
| 6,233,476 | B1 | 5/2001 | Strommer et al. |
| 6,301,496 | B1 | 10/2001 | Reisfeld |
| 6,609,027 | B2 | 8/2003 | Kroll et al. |
| 6,633,686 | B1 | 10/2003 | Bakircioglu et al. |
| 6,728,562 | B1 | 4/2004 | Budd et al. |
| 6,751,492 | B2 | 6/2004 | Ben-Haim |
| 6,978,168 | B2 | 12/2005 | Beatty et al. |
| 7,197,354 | B2 | 3/2007 | Sobe |
| 7,263,397 | B2 | 8/2007 | Hauck et al. |
| 7,276,064 | B2 | 10/2007 | Paul et al. |
| 7,338,486 | B2 | 3/2008 | Sliwa et al. |
| 7,386,339 | B2 | 6/2008 | Strommer et al. |
| 7,505,809 | B2 | 3/2009 | Strommer et al. |
| 7,697,973 | B2 | 4/2010 | Strommer et al. |
| 7,881,769 | B2 | 2/2011 | Sobe |
| 8,016,764 | B1 | 9/2011 | Shelchuk |
| 8,196,292 | B2 | 6/2012 | Noren et al. |
| 8,849,381 | B2 | 9/2014 | Mason et al. |
| 9,162,067 | B1 * | 10/2015 | Farazi .................... A61B 5/686 |
| 2003/0093067 | A1 | 5/2003 | Panescu |
| 2003/0233039 | A1 | 12/2003 | Shao et al. |
| 2005/0154282 | A1 | 7/2005 | Li et al. |
| 2006/0245536 | A1 | 11/2006 | Boing |
| 2007/0055142 | A1 | 3/2007 | Webler et al. |
| 2007/0073179 | A1 | 3/2007 | Afonso et al. |
| 2007/0100332 | A1 | 5/2007 | Paul et al. |
| 2007/0106146 | A1 | 5/2007 | Altmann et al. |
| 2007/0181139 | A1 | 8/2007 | Hauck |
| 2007/0244479 | A1 | 10/2007 | Beatty et al. |
| 2007/0270705 | A1 | 11/2007 | Starks |
| 2007/0299352 | A1 | 12/2007 | Harlev |
| 2008/0009758 | A1 | 1/2008 | Voth |
| 2008/0091193 | A1 | 4/2008 | Kauphusman et al. |
| 2008/0190438 | A1 | 8/2008 | Harlev |
| 2009/0163904 | A1 | 6/2009 | Miller et al. |
| 2009/0171345 | A1 | 7/2009 | Miller et al. |
| 2009/0275828 | A1 | 11/2009 | Shachar et al. |
| 2009/0306732 | A1 | 12/2009 | Rosenberg et al. |
| 2010/0168550 | A1 | 7/2010 | Byrd et al. |
| 2010/0268059 | A1 | 10/2010 | Ryu |
| 2011/0190593 | A1 * | 8/2011 | McNair .................... A61B 5/00 600/300 |
| 2011/0208038 | A1 | 8/2011 | Konofagou et al. |
| 2011/0243401 | A1 | 10/2011 | Zabair et al. |
| 2012/0184863 | A1 | 7/2012 | Harlev et al. |
| 2013/0222415 | A1 | 8/2013 | Vilsmeier |
| 2013/0272592 | A1 | 10/2013 | Eichler et al. |
| 2015/0045867 | A1 | 2/2015 | Krishnan et al. |
| 2015/0133802 | A1 | 5/2015 | Nabutovsky et al. |
| 2015/0141765 | A1 | 5/2015 | Razavi et al. |
| 2015/0141858 | A1 | 5/2015 | Razavi et al. |
| 2017/0042481 | A1 | 2/2017 | Olson |

FOREIGN PATENT DOCUMENTS

| | | |
|---|---|---|
| EP | 2 757 528 A1 | 7/2014 |
| WO | 97/24981 | 7/1997 |
| WO | 2012/090148 A1 | 7/2012 |

OTHER PUBLICATIONS

USPTO, "Non-Final Office Action for U.S. Appl. No. 14/703,735", dated Jan. 12, 2017.
USPTO, "Non-Final Office Action for U.S. Appl. No. 14/703,744", dated Jan. 13, 2017.
University of California, San Francisco, "History of AF Ablation", https://cardiology.ucsf.edu/care/clinical/electro/ablation_hist.html, accessed on Jan. 17, 2017.
Final Office Action dated Jan. 22, 2016; Related U.S. Appl. No. 14/270,176.
Non-Final Office Action dated Feb. 8, 2016; Related U.S. Appl. No. 14/270,181.
Non-Final Office Action dated Dec. 11, 2015; Related U.S. Appl. No. 14/703,460
Non-Final Office Action dated Sep. 30, 2015; Related U.S. Appl. No. 14/270,181.
Notice of Allowance dated Dec. 8, 2015; Related U.S. Appl. No. 12/347,216.
Notice of Allowance dated Oct. 27, 2015; Related U.S. Appl. No. 14/328,523.
Notice of Allowance dated Jun. 22, 2015; Related U.S. Appl. No. 14/328,523.
Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/US2015/028206 (dated Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731, filed Jun. 30, 1998 for "Chamber Mapping System".
Advisory Action dated Aug. 10, 2015; Related U.S. Appl. No. 12/347,216.
Amendment filed Jun. 25, 2015; Related U.S. Appl. No. 12/347,216.
Final Office Action dated May 4, 2015; Related U.S. Appl. No. 12/347,216.
Amendment filed Dec. 18, 2014; Related U.S. Appl. No. 12/347,216.
Non-Final Office Action dated Oct. 2, 2014; Related U.S. Appl. No. 12/347,216.
Advisory Action dated May 1, 2014; Related U.S. Appl. No. 12/347,216.
Amendment filed Apr. 24, 2014; Related U.S. Appl. No. 12/347,216.
Applicant Interview Summary, dated Apr. 21, 2014; Related U.S. Appl. No. 12/347,216.
Final Office Action dated Feb. 25, 2014; Related U.S. Appl. No. 12/347,216.
Amendment filed Feb. 4, 2014; Related U.S. Appl. No. 12/347,216.
Non-Final Office Action dated Nov. 21, 2013; Related U.S. Appl. No. 12/347,216.
Amendment filed Oct. 29, 2012; Related U.S. Appl. No. 12/347,216.
Advisory Action dated Oct. 11, 2012; Related U.S. Appl. No. 12/347,216.
Amendment filed Oct. 1, 2012; Related U.S. Appl. No. 12/347,216.
Advisory Action dated Sep. 12, 2012; Related U.S. Appl. No. 12/347,216.
Amendment filed Aug. 28, 2012; Related U.S. Appl. No. 12/347,216.
Final Office Action dated Jun. 29, 2012; Related U.S. Appl. No. 12/347,216.
Amendment filed May 14, 2012; Related U.S. Appl. No. 12/347,216.
Interview Summary, dated Feb. 28, 2012; Related. U.S. Appl. No. 12/347,216.

(56) References Cited

OTHER PUBLICATIONS

Non-Final Office Action dated Feb. 13, 2012; Related U.S. Appl. No. 12/347,216.
USPTO, "Notice of Allowance for U.S. Appl. No. 14/270,176", dated May 20, 2016.
Notice of Allowance dated Feb. 25, 2016; Related U.S. Appl. No. 14/328,513.
Notice of Allowance dated Feb. 25, 2016; Related U.S. Appl. No. 14/703,760.
Non-Final Office Action dated Mar. 28, 2016; Related U.S. Appl. No. 14/703,749.
Notice of Allowance dated Apr. 19, 2016; Related U.S. Appl. No. 14/270,181.
USPTO, "Non-Final Office Action for U.S. Appl. No. 14/270,186", dated Feb. 27, 2017.
USPTO, "Non-Final Office Action for U.S. Appl. No. 14/703,757", dated Apr. 6, 2017.
Notice of Allowance dated Apr. 18, 20017; Related U.S. Appl. No. 14/703,749.
Notice of Allowance dated Jun. 2, 20017; Related U.S. Appl. No. 14/703,744.
St. Jude Medical, "EnSite Velocity Cardiac Mapping System, Model EE3300, v.4." Feb. 28, 2013, 238 pages.
Office Action dated Jul. 5. 2017; Related U.S. Appl. No. 14/270,191.
Notice of Allowance dated May 9, 2017; Related U.S. Appl. No. 14/703,749.

* cited by examiner

METHOD AND SYSTEM TO IDENTIFY MOTION DATA ASSOCIATED WITH CONSISTENT ELECTRICAL AND MECHANICAL BEHAVIOR FOR A REGION OF INTEREST

RELATED APPLICATION DATA

The present application claims priority to U.S. provisional application Ser. No. 61/906,305, titled "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION", which was filed on Nov. 19, 2013 and is expressly incorporated herein by reference in its entirety of the present application.

BACKGROUND OF THE INVENTION

Embodiments of the present disclosure generally relate to measuring cardiac motion, and more particularly to measuring cardiac motion using a cardiovascular navigation system.

A prevailing theory regarding response to cardiac resynchronization therapy (CRT) is that the therapy corrects mechanical dyssynchrony of the heart. Therefore, methods and systems have been proposed to accurately assess the dyssynchrony. The dyssynchrony information may be used to predict response to CRT as well as optimize LV lead placement and CRT programming parameters. Today, most methods to assess mechanical dyssynchrony involve echocardiography. However, in certain circumstances, conventional echocardiography techniques may experience errors that lead to inaccurate characterization of dyssynchrony. Further, questions still remain as to which specific approach(es) is(are) preferred for assessing dyssynchrony, with various indices being used with mixed success.

Today, various cardiovascular navigation systems exist. For example, the St. Jude Medical MediGuide™ (MDG) cardiovascular navigation system is a 3-D electromagnetic navigation system that provides real-time position and orientation information of sensors embedded in electrophysiologic tools. The MDG system is integrated with a fluoroscopic (or other diagnostic) imaging system and tracks the sensors continuously within an imaging volume defined by the fluoroscopic system, on both live and pre-recorded background diagnostic images.

Recently, it has been proposed to utilize the MDG system to characterize motion of the heart and to identify a desired (e.g., optimal) location for placement of a left ventricular (LV) lead for CRT. For example, the MDG system systematically records information associated with various endocardial and epicardial locations in the LV. Depending on the size of the heart and other factors during the procedure, there may be a multitude of locations at which the MDG system obtains motion recordings for each patient. These recordings then need to be analyzed to characterize motion and mechanical activation patterns in the LV.

However, cardiovascular navigation systems may experience inconsistencies in motion characterizations of the heart due to ectopic beats or catheter dislodgments. Ectopic beats and catheter dislodgement create electrical and/or mechanical measurement disturbances that in the measured signals are exhibited as inconsistent electrical rhythm and/or mechanical behavior. Cardiac events occurring during inconsistent electrical rhythm and/or mechanical behavior may exhibit unreliable motion characterization information. Methods and systems are needed to identify and filter out ectopic beats or beats occurring during catheter dislodgement such that the remaining beats exhibit consistent motion information that yields reliable motion characterization.

SUMMARY

In accordance with embodiments herein, a method is provided to identify consistent electrical and mechanical measurements from a compilation of electrical and motion data of a region of interest. The method includes simultaneously acquiring electrical sensor measurements from an electrical sensor and motion data from a motion sensor in contact with the region of interest, determining valid electrical waveforms from the electrical sensor measurements removing ectopic beat data from motion data, acquiring a position measurement of at least one motion sensor in contact with the region of interest, removing inconsistent motion characterization data based on at least two different coordinates, synchronizing the motion data, and determining an average motion characterization waveform for each map point.

Optionally, the method may have the electrical sensor measurements contain a QRS complex and/or electrical component indicative of local activation and electrode-tissue contact.

Optionally, the method may have the electrical sensor and motion sensor integrated into an electrophysiological sensor.

In accordance with embodiments herein, methods are provided that identify motion data associated with consistent electrical and mechanical behavior for a region of interest of the heart. The methods include acquiring electrical cardiac signals indicative of physiologic behavior of at least a portion of the heart over a plurality of cardiac cycles. The methods acquire motion data indicative of mechanical behavior of a motion sensor over the plurality of cardiac cycles to form a motion data collection, the motion data indicative of mechanical behavior of the region of interest when the motion sensor is in contact with the region of interest. The methods designate ectopic beats within the cardiac cycles based on the electrical cardiac signals, the ectopic beats producing electrically inconsistent (EI) data within the motion data collection. The methods further comprise identifying mechanically inconsistent (MI) data within the motion data collection based on irregular changes in the motion data. The methods remove at least a portion of the EI and MI data from the motion data collection based on the designating and identifying operations to form an electrically/mechanically consistent (EMC) motion data collection.

Optionally, the method may include removing the EI data associated with ectopic beats and removing motion data associated with at least a portion of neighboring beats that occurs at least one of before or after the ectopic beats. Alternatively or additionally, the method may include removing the MI data associated with the irregular changes and at least a portion of adjacent motion data that occurs at least one of before or after the irregular changes. Optionally, the method may include analyzing the motion data to identify changes in the motion data that exceed a predetermined threshold within a select period of time.

Alternatively or additionally, the method may include analyzing the motion data to identify at least one of sudden or non-periodic changes in the motion data, the at least one of sudden or non-periodic changes being identified as MI data. Optionally, the motion sensor may be located on a medical tool in contact with the region of interest, and the identifying operation analyzes a waveform representative of the motion data over time to identify waveform characteristics indicative of separation between the medical tool and the region of interest. Alternatively or additionally, the method may further comprise repeating the acquiring, designating, identifying and removing operations for each of multiple map points on the region of interest to form separate EMC motion data collections for each of the multiple map points.

Optionally, the acquiring, designating, identifying and removing operations may be performed for a select map point, the method further comprising determining a motion characterization waveform for the map point based on the EMC motion data collection and excluding the EI and MI data. Alternatively or additionally, the method may include the electrical cardiac signals defining a cardiac waveform. The designating operation includes parsing through the cardiac waveform to identify, as a characteristic representative of abnormal physiologic behavior, one or more of: when a peak amplitude of a QRS complex falls below a threshold amplitude; when a QRS complex has a double-peaked or flat R-wave; when consecutive R waves have an R-R interval that is longer or shorter than a select R-R interval by more than a cutoff value, and when a correlation score based on the morphology of the cardiac waveform is below a predetermined baseline.

Optionally, the method may comprise the motion data collection including motion data associated with X, Y and Z coordinates of a reference coordinate system, the identifying operation identifying MI data based on irregular changes in the motion data along one or more of the X, Y and Z coordinates.

In accordance with another embodiment, a system is provided to identify motion data associated with consistent electrical and mechanical behavior for a region of interest of the heart. The system comprises a processor. The system also comprises an electrical sensor configured to acquire electrical cardiac signals indicative of physiologic behavior of at least a portion of the heart over a plurality of cardiac cycles. The system also comprises a motion sensor on a medical tool, the motion sensor configured to acquire motion data indicative of mechanical behavior of the motion sensor over the plurality of cardiac cycles to form a motion data collection, the motion data indicative of mechanical behavior of the region of interest when the motion sensor is in contact with the region of interest. The system also comprises a local storage medium storing program instructions accessible by the processor. The system includes the processor being responsive to execution of the program instructions. The process is configured to designate ectopic beats within the cardiac cycles based on the electrical cardiac signals, the ectopic beats producing electrically inconsistent (EI) data within the motion data collection. The processor is also configured to identify mechanically inconsistent (MI) data within the motion data collection based on irregular changes in the motion data; and remove at least a portion of the EI and MI data from the motion data collection based on the designating and identifying operations to form an electrically/mechanically consistent (EMC) motion data collection.

Optionally, the system may include the processor being configured to remove the EI data associated with ectopic beats and remove motion data associated with at least a portion of neighboring beats that occur at least one of before or after the ectopic beats. Alternatively or additionally, the system may include the processor being configured to remove the MI data associated with the irregular changes and at least a portion of adjacent motion data that occurs at least one of before or after the irregular changes. Optionally, the system may include the processor being configured to analyze the motion data to identify changes in the motion data that exceed a predetermined threshold within a select period of time.

Alternatively or additionally, the system may include the processor being configured to analyze the motion data to identify at least one of sudden or non-periodic changes in the motion data, the at least one of sudden or non-periodic changes being identified as MI data. Optionally, the system may include the motion sensor being located on a medical tool in contact with the region of interest and the processor being configured to analyze a waveform representative of the motion data over time to identify waveform characteristics indicative of separation between the medical tool and the region of interest. Alternatively or additionally, the system may include the processor being configured to repeat the acquiring, designating, identifying and removing operations for each of multiple map points on the region of interest to form separate EMC motion data collections for each of the multiple map points.

Alternatively or additionally, the system may include the processor being configured to: perform the acquiring, designating, identifying and removing operations for a select map point; and determine a motion characterization waveform for the map point based on the EMC motion data collection and exclude the EI and MI data. Optionally, the system may include the electrical cardiac signals defining a cardiac waveform, and the processor being configured to parse through the cardiac waveform to identify, as a characteristic representative of abnormal physiologic behavior, one or more of: when a peak amplitude of a QRS complex falls below a threshold amplitude; when a QRS complex has a double-peaked or flat R-wave; when consecutive R waves have an R-R interval that is longer or shorter than a select R-R interval by more than a cutoff value, and when a correlation score based on the morphology of the cardiac waveform is below a predetermined baseline.

Optionally, the system may include the motion data collection including motion data associated with X, Y and Z coordinates of a reference coordinate system, the processor being configured to identify MI data based on irregular changes in the motion data along one or more of the X, Y and Z coordinates.

DETAILED DESCRIPTION

Figure 1:
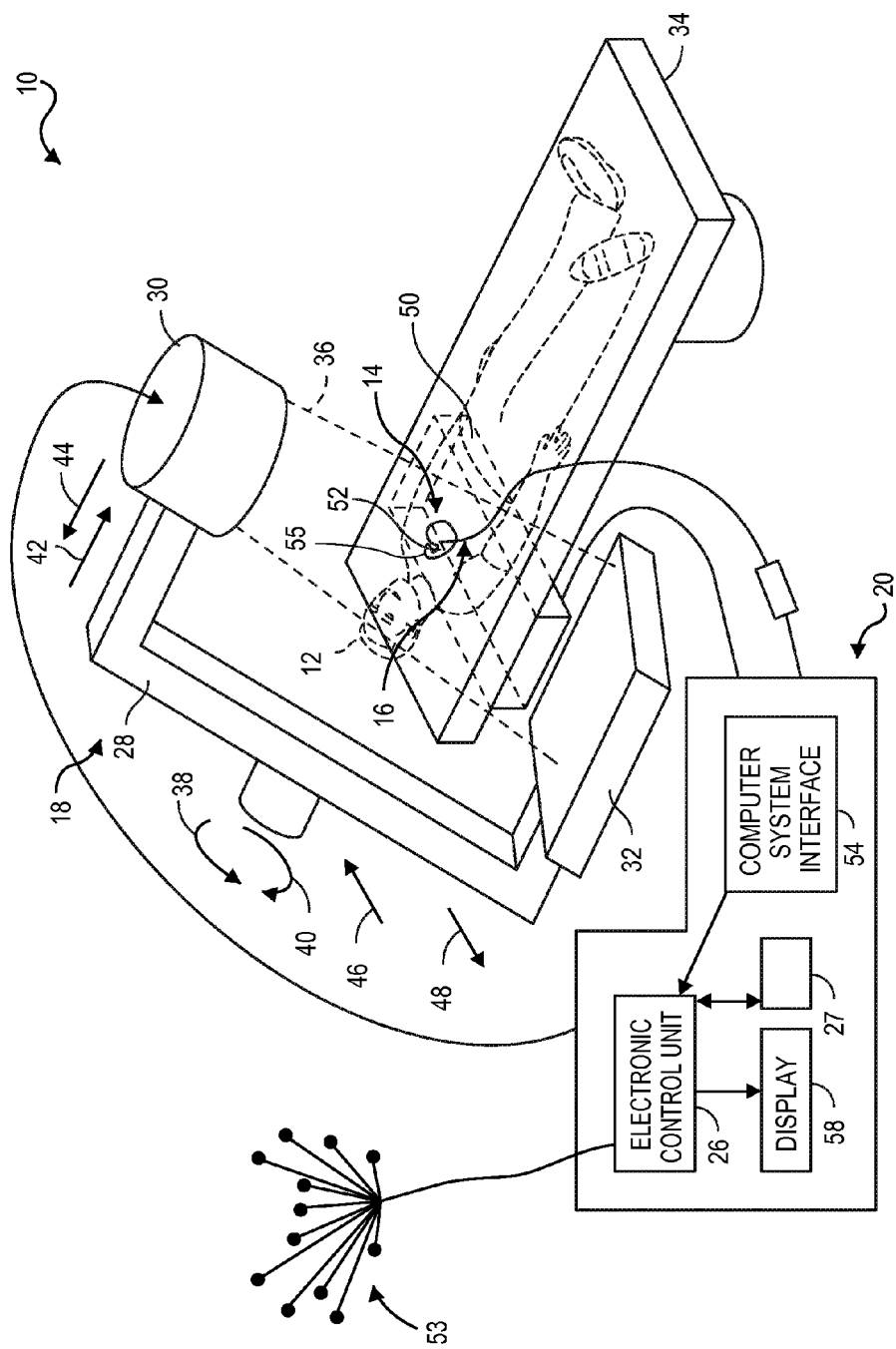
FIG. 1 illustrates an imaging and navigation system of an exemplary embodiment.

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Embodiments herein may be implemented with, and/or utilize aspects of, the methods and system described in the following applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. patent application Ser. No. 14/270,181, titled "METHOD AND SYSTEM TO CHARACTERIZE MOTION DATA BASED ON NEIGHBORING MAP POINTS", filed May 5, 2014, now U.S. Pat. No. 9,364,170, U.S. patent application Ser. No. 14/270,186, titled "METHOD AND SYSTEM FOR CALCULATING STRAIN FROM CHARACTERIZATION DATA OF A CARDIAC CHAMBER", filed May 5, 2014, published as U.S. Pub. No. 2015/0313480, U.S. patent application titled "METHOD AND SYSTEM FOR DISPLAYING A THREE DIMENSIONAL VISUALIZATION OF CARDIAC MOTION", filed May 5, 2014, now U.S. Pat. No. 9,380,940, all of which are expressly incorporated herein by reference in their entirety.

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

FIG. 1 illustrates a cardiovascular navigation system 10, of an embodiment, for use in imaging an anatomical region of a patient 12 such as a heart 14. A medical tool 16 is placed within the anatomical region, such as for example, an electrophysiological (EP) mapping catheter or a catheter generally described or shown in U.S. Pat. No. 7,881,769, the entire disclosure of which is incorporated herein by reference. The medical tool 16 includes a plurality of motion sensors 52 that may be placed on the endocardial or epicardial surface of the left ventricle of the heart 14. The motion sensors 52 may be attached to the distal or proximal end of the medical tool 16, or any point in between. The motion sensors 52 measure a position and an orientation of the medical tool 16, and are transmitted to an electronic control unit (ECU) 26. Optionally, the motion sensors 52 may be used concurrently and/or integrated with electrical sensors to measure an electrical potential or electric current of biological cells and tissues. The motion sensors in contact with the region of interest measuring the position and electrical sensors measuring the electrical potential or electric current of the region of interest. Optionally, ECU 26 may receive the position and electrical sensor measurements simultaneously from the motion sensors and electrical sensors. For example, the motion sensors 52 may be positioned by the medical tool 16 to measure the electrical potential along a portion of the wall of the heart 14. It should be understood, however, that the motion sensors 52 could be used in a variety of anatomical regions within the heart 14 or other organs in which motion characterization may be of interest.

System 10 may include an imaging system 18 and a medical device navigation system 20. The system 20 includes a local storage medium 27 that stores program instructions to direct the ECU 26 to perform various operations including the operations set forth in FIG. 3. The system 10 may also include a registration system for registering a group of images of the anatomical region of patient 12 in a navigation coordinate system of the navigation system 20 as generally described and shown in U.S. Patent Publication 2013/0272592 and International Pub. No. WO 2012090148, the entire disclosure of which is incorporated herein by reference.

The imaging system 18 may be provided to acquire images of heart 14 or another anatomical region of interest and comprises a fluoroscopic imaging system in the illustrated embodiment. Additionally or alternatively, rather than a fluoroscopic imaging system, a computed tomography (CT) imaging systems, three-dimensional radio angiography (3DRA) systems and the like may be used. Although the imaging system 18 is described herein for an embodiment of the invention, the imaging system 18 is not required for the inventive subject matter described within this application.

The imaging system 18 may include a C-arm support structure 28, a radiation emitter 30, and a radiation detector 32. Emitter 30 and detector 32 are disposed on opposite ends of support structure 28 and disposed on opposite sides of patient 12 as patient 12 lays on an operation table 34. Emitter 30 and detector 32 define a field of view 36 and are positioned such that the field of view 36 includes the anatomical region of interest as patient 12 lays on operation table 34. The operation table 34 may be configured to move in a table up direction and a table down direction with respect to the emitter 30 or detector 32. Additionally or alternatively, the operation table 34 may be configured to move in an inward direction and an outward direction with respect to the C-arm support structure 28.

Imaging system 18 is configured to capture images of anatomical features and other objects within field of view 36. The C-arm support structure 28 may have freedom to rotate about the patient as shown by lines 38, 40. The C-arm support structure 28 may also have freedom to slide along lines 42, 44 (i.e. along the cranio-caudal axis of patient 12) and/or along lines 46, 48 (i.e. perpendicular to the craniocaudal axis of patient 12). Rotational and translational movement of support structure 28 yields corresponding rotational and translational movement of field of view 36.

Imaging system 18 may acquire a group of images of an anatomical region of patient 12 by first shifting along lines 42, 44, 46, 48 to place the anatomical region of interest within the field of view 36. Second, the C-arm support structure 28 may rotate radiation emitter 30 and radiation detector 32 about patient 12, keeping the anatomical region within field of view 36. Imaging system 18 may capture images of the anatomical region as support structure 28 rotates, providing a group of two-dimensional images of the anatomical region from a variety of angles. The group of images may be communicated to ECU 26 for image processing and display. The group of images may comprise a sequence of images taken over a predetermined time period.

Navigation system 20 may be provided to determine the position and orientation of medical tool 16 within the body of patient 12 and to permit a clinician to navigate the medical tool 16 within the body. In the illustrated embodiment, system 20 comprises a magnetic navigation system in which magnetic fields are generated in the anatomical region and motion sensors 52 associated with tool 16 generate an output that changes responsive to the position of the sensors within the magnetic field. System 20 may comprise, for example, the systems generally shown and described in, for example, U.S. Pat. Nos. 6,233,476, 7,197,354, 7,386,339, and 7,505,809 all of which are incorporated by reference in their entirety. Although a magnetic navigation system is shown in the illustrated embodiment, it should be understood that the invention could find use with a variety of navigation systems including those based on the creation and detection of axes specific electric fields. Navigation system 20 may include a transmitter assembly 50.

The transmitter assembly 50 is conventional in the art and may include a plurality of coils arranged orthogonally to one another to produce a magnetic field in and/or around the anatomical region of interest. It should be noted that, although transmitter assembly 50 is shown under the body of patient 12 and under table 34 in FIG. 1, transmitter assembly 50 may be placed in another location, such as attached to radiation emitter 30 or detector 32, from which the magnetic field generators can project a magnetic field in the anatomical region of interest. In accordance with certain embodiments of the invention the transmitter assembly 50 is within the field of view 36. The ECU 26 may control the generation of magnetic fields by transmitter assembly 50.

The motion sensors 52 are configured to generate an output dependent on the relative position and orientation of motion sensors 52 within the field generated by transmitter assembly 50. In FIG. 1, the motion sensor 52 and medical tool 16 are shown disposed around the heart 14. As medical tool 16 is guided to and through the region of interest, the navigation system 20 determines the location of the motion sensors 52 in the generated field, and thus the position of medical tool 16 as well. The navigation system 20 further determines a navigation coordinate such as a Cartesian coordinate (e.g., (X, Y, Z)), of the navigation coordinate system.

One or more patient reference sensors (not shown) are on the body of the patient 12, for example, on the chest. The patient reference sensors (PRS) measure a displacement and orientation of the patient reference sensors relative to a predetermined reference point, such as, the motion sensors 52 or the transmitter assembly 50.

Figure 2:
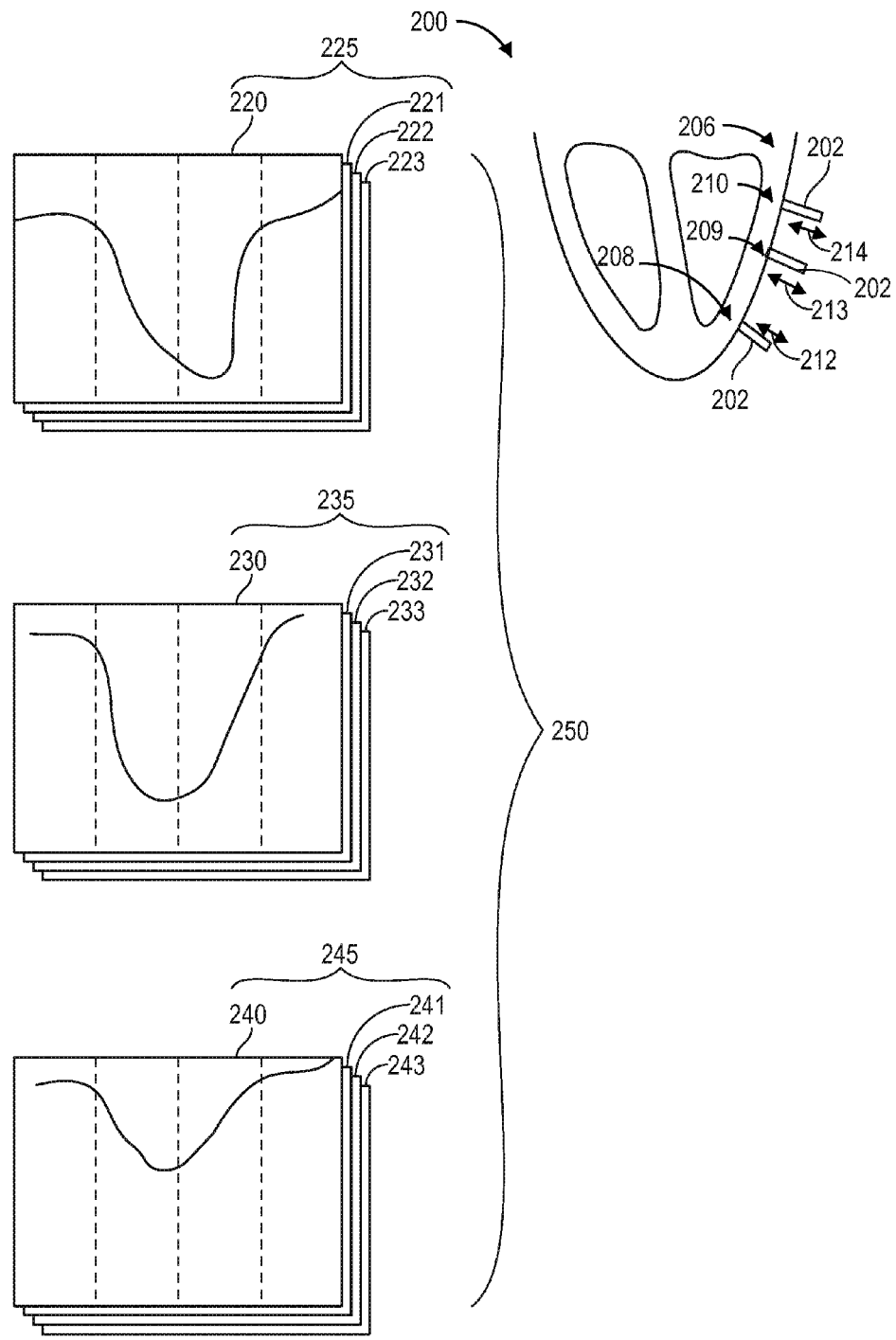
FIG. 2 illustrates an embodiment of collecting motion data using a cardiovascular navigation system exhibited by a heart.

FIG. 2 illustrates a graphical representation of the process for collecting of motion data from motion sensors (e.g., the motion sensors 52) on a tool 202 (e.g., catheter, the medical tool 16). FIG. 2 illustrates a portion of a heart 200 having a heart wall 206, for which it is desirable to measure motion and determine mechanical behavior. The heart wall 206 may be separated into map points of interest 208-210. The example of FIG. 2 shows three map points of interest 208-210 along the wall of the left ventricle. Optionally more or fewer map points of interest may be designated. The tool 202 is positioned directly against the heart endocardial or epicardial wall at one or more points within each map point of interest 208-210. In the example of FIG. 2, the tool 202 is shown positioned against a point of interest for each map point 208-210 at different points in time. For example, the tool 202 is positioned, during a first measuring operation, at map point 208 while collecting motion data associated with movement (e.g., along the arrow 212) at the map point 208. The movement may be in various linear, transverse, or rotational directions. Next, the tool 202 may be positioned, during a second measuring operation, at map point 209 while collecting motion data associated with movement (e.g., along the arrow 213) at the map point 209. Next, the tool 202 is positioned, during a third measuring operation, at map point 210 while collecting motion data associated with movement (e.g., along the arrow 214) at the map point 210.

The position of the tool 202 is continuously monitored by the navigation system (e.g., the system 20) to obtain sets of motion data associated with each map point 208-210. Optionally, a map point specific motion data (PSMD) collection is obtained for at least one cardiac cycle. In FIG. 2, a PSMD collection 220 is collected during one cardiac cycle while the tool 202 is held against the LV wall at map point 208. The tool 202 is held against the LV wall at map point 208 for multiple heart beats thereby generating multiple PSMD collections 220-223 (e.g., for 4 consecutive heart beats). Optionally, PSMD collections may be collected for more than 4 heart beats. The PSMD collections 220-223 associated with map point 208 may be grouped to form a collection 225 of PSMD collections 220-223 associated with a single map point 208.

Once a desired amount of motion data is collected for map point 208, the tool 202 is moved to a next desired position, such as map point 209. Next, the data collection process is repeated to obtain PSMD collections 230-233 that include motion data indicative of an amount and direction of motion experienced by map point 209 over a corresponding number of heart beats (e.g., cardiac cycles). Once a desired amount of motion data is collected for map point 209, the tool 202 is moved to a next desired position such as at map point 210. Next, the data collection process is repeated to obtain PSMD collections 240-243 that include motion data indicative of an amount and direction of motion experienced by map point 210 over a corresponding number of heart beats (e.g., cardiac cycles). The PSMD collections 230-233 and 240-243, which are associated with map points 209 and 210, may, be grouped to form collections 235 and 245, respectively, associated with single map points 209 and 210. The plurality of PSMD collections 220-243 for all heart wall map points of interest collectively defines a motion data collection 250.

Optionally, multiple tools 202 or a tool with multiple independently movable position sensors may be used to simultaneously collect motion data for multiple map points. Optionally, more map points of the heart wall may be studied to collect additional PSMD collections of motion data. For example, the walls of the RV, RA, and/or LA may also be divided into map points, for which motion data are collected.

The navigation system 20 collects the motion data from one or more tools 202. The tool(s) 202 may be held in contact with the epicardial wall and/or endocardial wall of the heart. The motion data 250 are preprocessed to compensate for changes in tool 202 position, such as due to movement of the imaging equipment (e.g., c-arm movement), due to patient movement, and/or due to respiration. The motion data 250 may be converted to patient-specific cardiac coordinates. The motion data 250 may be analyzed to identify and remove non-ectopic beats and to eliminate beats with abrupt mechanical movement. Optionally, the motion data 250 may include averages of motion data collected over multiple heart beats (cardiac cycles). For example, the PSMD collections 220-223 may be combined through averaging or otherwise. Optionally, the motion data 250 that is utilized in connection with embodiments described hereafter, may include information indicative of a radial component of wall movement, and/or may include information indicative of a longitudinal component of wall movement. Optionally, the motion data may include information associated with 3-dimensional movement calculated as a 3-D distance from an initial position at a select starting point in the cardiac cycle, such as the R wave or local electrical activation time.

Electrical sensors 53 are coupled to the ECU 26 of the navigation system 20 to obtain electrical measurements of cardiac activity to the patient. The sensors 53 may represent ECG leads that are attached to the patient's skin, electrical sensors on catheters that are inserted into the heart collecting IEGM signals and the like. Optionally, the electrical cardiac signals received by the ECU 26 may define a cardiac waveform of the heart.

The ECU 26 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 26 may receive a plurality of input signals including signals generated by medical tool 16, imaging system 18, the motion sensors 52, an operator system interface 54, and the patient reference sensors and generate a plurality of output signals including those used to control tool 16, imaging system 18, and/or the display 58. The operator system interface 54 may include a keyboard, a keypad, buttons, a touchscreen, a monitor, a mouse, and the like. ECU 26 may also receive an input signal from an organ monitor (not shown), such as an ECG monitor, and sort or segregate images from imaging system 18 based on a timing signal of a monitored organ. For example, ECU 26 may sort images based on the phase of the patient's cardiac cycle at which each image was collected, as more fully described in U.S. Pat. No. 7,697,973, which is hereby incorporated by reference in its entirety.

The ECU 26 includes one or more processors that are coupled to local storage medium 27 storing program instructions accessible by the processors. Responsive to execution of the program instructions, the processor(s) of the ECU 26 is configured to: designate ectopic beats within the cardiac cycles based on the electrical cardiac signals, the ectopic beats producing electrically inconsistent (EI) data within motion data collection; identify mechanically inconsistent (MI) data within the motion data collection based on irregular changes in the motion data; and remove at least a portion of the EI and MI data from the motion data collection based on the designating and identifying operations to form an electrically/mechanically consistent (EMC) motion data collection. Optionally, the processor(s) of the ECU 26 is configured to remove the EI data associated with ectopic beats and remove motion data associated with at least a portion of neighboring beats that occur at least one of before or after the ectopic beats. Optionally, the processor is configured to remove the MI data associated with the irregular changes and at least a portion of adjacent motion data that occurs at least one of before or after the irregular changes.

Additionally or alternatively, the processor(s) of the ECU 26 is configured to analyze the motion data to identify changes in the motion data that exceed a predetermined threshold within a select period of time. Additionally or alternatively, the processor(s) of the ECU 26 is configured to analyze the motion data to identify at least one of sudden or non-periodic changes in the motion data, the at least one of sudden or non-periodic changes being identified as MI data. The motion sensor is located on a medical tool in contact with the region of interest. Additionally or alternatively, the processor(s) of the ECU 26 is configured to analyze a waveform representative of the motion data over time to identify waveform characteristics indicative of separation between the medical tool and the region of interest.

Additionally or alternatively, the processor(s) of the ECU 26 is configured to repeat the acquiring, designating, identifying and removing operations for each of multiple map points on the region of interest to form separate EMC motion data collections for each of the multiple map points. Additionally or alternatively, the processor(s) of the ECU 26 is configured to: perform the acquiring, designating, identifying and removing operations for a select map point; and determine a motion characterization waveform for the map point based on the EMC motion data collection and exclude the EI and MI data. Additionally or alternatively, the processor(s) of the ECU 26 is configured to parse through the cardiac waveform to identify, as a characteristic representative of abnormal physiologic behavior, one or more of: i) when a peak amplitude of a QRS complex falls below a threshold amplitude; ii) when a QRS complex has a double-peaked or flat R-wave; iii) when consecutive R waves have an R-R interval that is longer than a select R-R interval by more than a cutoff value. The motion data collection includes motion data associated with X, Y and Z coordinates of a reference coordinate system. Additionally or alternatively, the processor(s) of the ECU 26 is configured to identify MI data based on irregular changes in the motion data along one or more of the X, Y and Z coordinates.

At least one technical effect of at least one portion of the methods and systems described herein includes i) acquiring electrical sensor measurements from an electrical sensor and motion data from a motion sensor in contact with a region of interest, ii) determining valid electrical waveforms from the electrical sensor measurements and removing ectopic beat data from motion data, iii) acquiring a position measurement of the motion sensor, iv) analyzing the position data and removing inconsistent motion data based on at least two different position coordinates, v) synchronizing the motion data, and vi) determining an average motion characterization waveform for each map point.

At least one technical effect of at least one portion of the methods and systems described herein includes a method and/or system that identifies motion data associated with consistent electrical and mechanical behavior for a region of interest of the heart. Alternatively, the method and/or system acquires electrical cardiac signals indicative of physiologic behavior of at least a portion of the heart over a plurality of cardiac cycles. Further, the method and/or system acquires motion data indicative of mechanical behavior of a motion sensor over the plurality of cardiac cycles to form a motion data collection, the motion data indicative of mechanical behavior of the region of interest when the motion sensor is in contact with the region of interest. The designating ectopic beats within the cardiac cycles may be based on the electrical cardiac signals, the ectopic beats producing electrically inconsistent (EI) data within the motion data collection. Optionally the method and/or system may further comprise identifying mechanically inconsistent (MI) data within the motion data collection based on irregular changes in the motion data. Optionally, the method and/or system may include removing at least a portion of the EI and MI data from the motion data collection based on the designating and identifying operations to form an electrically/mechanically consistent (EMC) motion data collection.

Figure 3:
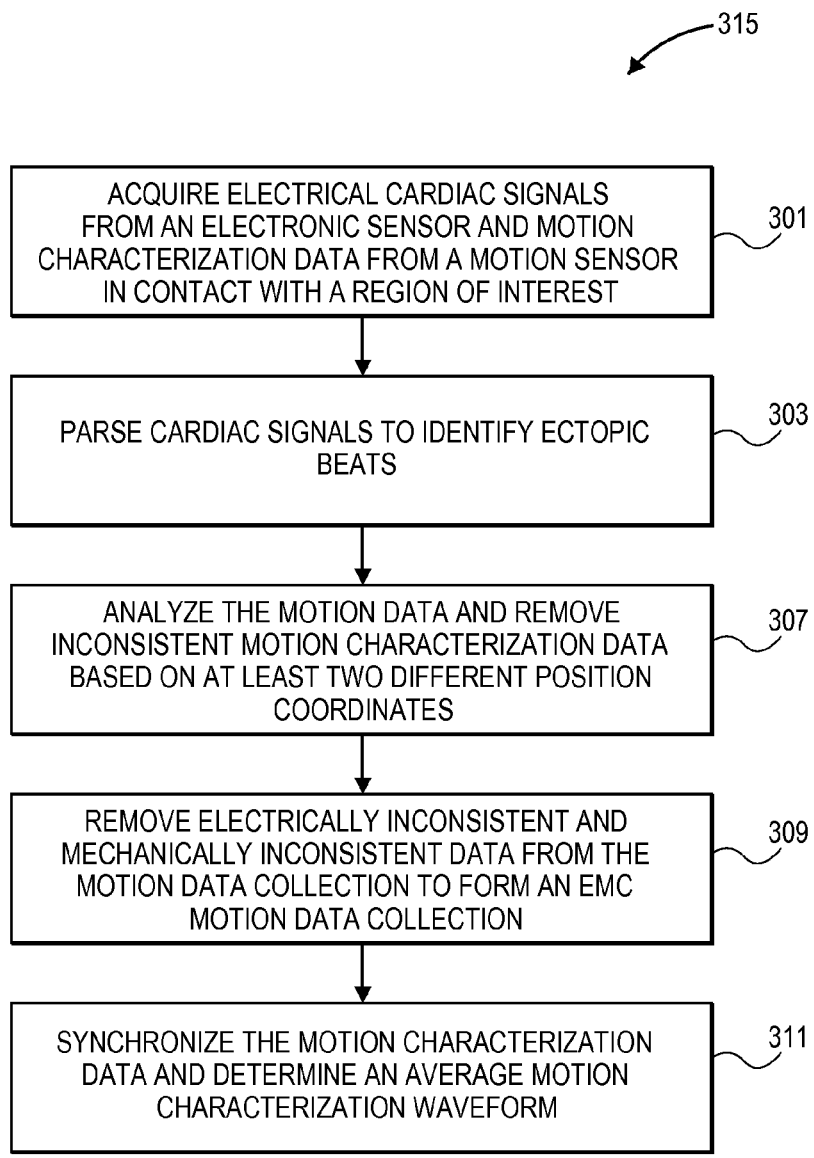
FIG. 3 illustrates a method to identify consistent electrical and mechanical measurements from a compilation of electrical and motion data of a region of interest.

FIG. 3 illustrates a flowchart of a method 315 to identify consistent electrical and mechanical behavior over cardiac cycles using a cardiovascular navigation system (e.g., 10). The method 315 may be implemented as a software algorithm, package, or system that directs one or more hardware circuits or circuitry to perform the actions described herein. For example, the operations of the method 315 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At 301, the method acquires electrical cardiac signals indicative of physiologic behavior of at least a portion of the heart over a plurality of cardiac cycles, and simultaneously acquires motion data indicative of mechanical behavior of a motion sensor over the same plurality of cardiac cycles to form a motion data collection. The electrical cardiac signals and motion data are temporarily aligned with corresponding electrical and mechanical events/features being sensed and recorded in a time-aligned manner. The electrical cardiac signals may be stored as part of, or in connection with, the motion data collection. The motion data is indicative of mechanical behavior of the region of interest when the motion sensor is in contact with the region of interest. For example, at 301, the electrical sensor 53 acquires electrical sensor measurements and the motion sensor 52 acquires the motion data while in contact with the region of interest. The motion data characterizes motion at the medical tool. The electrical sensor measurements may represent cardiac signals that are conventionally utilized to monitor electrical activity of a region of interest of a patient, such as the heart 14. The electrical signal may represent a 12-lead surface electrocardiogram (ECG), body surface mapping (BSM), a subcutaneous ECG, a uni- or bi-polar intracardiac electrograms (IEGMs) or the like. The electrical sensor 53 may be surface ECG leads, or an IEGM sensor on a catheter, such as the medical tool 16, placed in the coronary sinus (CS), right ventricular (RV apex), or the like. The electrical sensor measurements and motion data are received by the ECU 26 and stored in local storage medium 27.

At 303, the method parses through the cardiac signals and designates ectopic beats within the cardiac cycles based on the electrical cardiac signals. The ectopic beats produce electrically inconsistent (EI) data within the motion data collection. The electrical cardiac signals may define a cardiac waveform, where the method includes parsing through the cardiac waveform to identify a characteristic(s) representative of abnormal physiologic behavior. For example, the characteristic may be one or more of: when a peak amplitude of a QRS complex falls below a threshold amplitude; when a QRS complex has a double-peaked or flat R-wave; when consecutive R waves have an R-R interval that is longer than a select R-R interval by more than a cutoff value. Based on the characteristic of interest, ECU 26 determines whether portions of the measured cardiac signals represent valid or invalid beats (e.g., based on the waveform shape, amplitude, timing, duration, and the like). The ectopic beat represents a disturbance of the cardiac rhythm in which the beat arises outside the region of the heart muscle ordinarily responsible for impulse formation. The ectopic beats may have a lower or higher peak amplitude relative to the normal R-wave amplitude of a normal QRS complex. The characteristic indicating ectopic beats may be identified using a threshold amplitude that is compared to the electrical sensor measurements. For example, the ECU 26 may receive the electrical sensor measurements 401, shown in FIG. 4, from the electrical sensor 53, such as a 12-lead surface ECG. For normal beats, the QRS peak has a very sharp peak or sharp slope. The electrical sensor measurement 401 has an inverted morphology for extra-systolic or pre-mature ectopic beats 405, such that the QRS peak has a relatively distinct lower amplitude.

Figure 4:
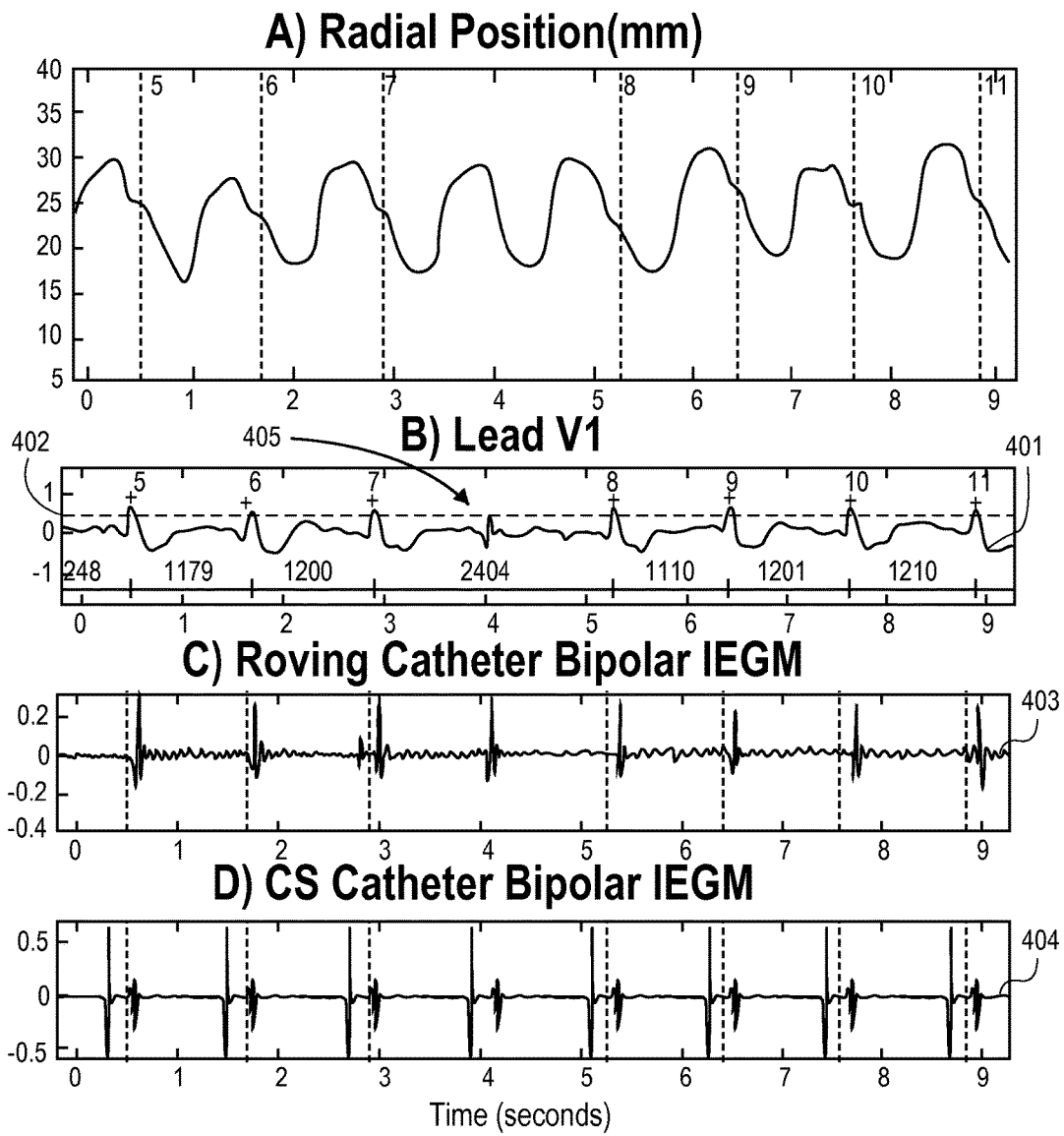
FIG. 4 illustrates a timing diagram showing electrical and motion data of an imaging and navigation system.

In at least one embodiment, to locate local peaks in the electrical sensor measurements 401, the ECU 26 compares the electrical sensor measurements 401 against a predetermined threshold amplitude 402 and a minimum time distance between two consecutive peaks (e.g., 800 ms). The ECU 26 determines that a sample point above the threshold amplitude 402 represents a peak when the measurements 401 change in slope from positive to zero or negative in a consecutive select series of sample points. In the example of FIG. 4, the ECU 26 detects a peak of the R-wave on all beats except the ectopic beat 405. Further, the ECU 26 may exclude the immediate neighbors of an ectopic beat (e.g., 405) to ensure that ectopic beats 405, which can affect cardiac biomechanics for a couple of cycles, do not introduce variability in the motion data. Optionally, the ECU 26 may determine whether one or more measured electrical cardiac signals from the electrical sensor measurements 401 (e.g., from surface ECG leads and intra-cardiac signals), during a cardiac cycle, represent an ectopic beat 405 by comparing a morphology (e.g., structure, slope, peaks) of the measured electrical cardiac signal against a template electrical cardiac waveform. For example, the template electrical cardiac waveform may be an average of a plurality of known or acceptable R-wave or cardiac beats. The ECU 26 may calculate a correlation score by comparing the measured electrical cardiac signals against the template electrical cardiac waveform. The correlation score representing a degree of similarity between the morphology of the measured electrical cardiac signal and that of the template electrical cardiac waveform. Once the correlation score is calculated, the ECU 26 may compare the correlation score with a predetermined baseline to determine whether an ectopic beat is present in the measured electrical cardiac signals. For example, if the correlation score is less than 0.8 the ECU 26 may determine that the measured electrical cardiac signal includes an ectopic beat. If the correlation score is greater than or equal to 0.8, the ECU 26 may determine that an ectopic beat is not included in the measured electrical cardiac signal. It should be noted that in other embodiments the predetermined base line may be greater than or less than 0.8. Additionally or alternatively, the ECU 26 may calculate an average of the one or more measured electrical cardiac signals, which will be compared with the template electrical cardiac waveform.

Optionally, abrupt changes in neighboring cycle lengths, instead of amplitudes, can be used to detect an ectopic beat of the electrical sensor measurements. For example, the ECU 26 may determine two consecutive R-R intervals are calculated from three consecutive R waves such that the second R-R interval is longer than the first R-R interval by more than a select interval limit or cutoff value (e.g. 100 ms). The middle beat will be declared by the ECU 26 to be an ectopic beat and all three consecutive R waves will be excluded from further analysis. Additionally or alternatively, each cycle length may be compared to a mean of several previous cycle lengths, such that if the current beat exhibits an R-to-R interval that exceeds the mean by a select amount (e.g. by more 100 ms), the current beat will be classified as an ectopic beat and the ectopic beat along with preceding and succeeding beats before and after the ectopic beat are excluded from further analysis.

In embodiments, optionally, the electric sensor 53 may be used in conjunction with other electrical sensors to determine the electrical integrity of a given cardiac beat. For example, a bipolar IEGM signal 403 may be measured by an IEGM sensor 55 that is located on the medical tool 16. The IEGM sensor 55 may be used for ensuring a consistent level of contact of the medical tool 16 with the cardiac tissue of interest, such as the heart 14, by ensuring consistent amplitude and morphology over several beats of the electrical signal. Further, based on the location of the medical tool 16, the IEGM sensor 55 may detect activity from cardiac tissue that is close to another chamber thereby exhibiting distinct peaks in the IEGM sensed signal that are earlier or later than the primary activation peak. The ECG and IEGM signals from sensors 53 and 55 may be correlated to line up in timing with the neighboring chamber's activation time. For instance, in the case of LV mapping, the bipolar IEGM signal measured from the IEGM sensor 53 of the medical tool 16 may depict signals from the left atrium at map points close to the mitral annulus. The signal may exhibit two distinct peaks with the atrial contribution occurring much earlier around the time of a surface ECG's P-wave. Additionally, the ratio of peak amplitudes can be used to quantify the relative position between atrial and ventricular chambers, such that if the contribution from the chamber of interest is significantly lower than the neighboring chamber by a pre-determined threshold, the corresponding beat(s) or location(s) are excluded from further analysis.

In embodiments, optionally, a bipolar IEGM signal 404 may be measured when the medical tool 16 (e.g., by the sensor 55 is placed at certain anatomical locations such as the coronary sinus. The signal 404 may be used to analyze the atrial and ventricular signals for the cardiac cycle or beat of interest. For example, the bipolar IEGM signal 404 may show two distinct peaks with one coming from atrial activation that lines up in time with the P-wave on the surface ECG signals and the other coming from a ventricular activation that lines up in time with the QRS complex on the surface ECG signals. The delay between the two peaks is indicative of the A-V interval. A shortening in the AV interval may indicate the presence of a premature ventricular contraction (PVC), which is one type of ectopic beat.

In embodiments, optionally, a secondary electrical sensor, for example a surface ECG or intra-cardiac signal, may be used as an additional signal to test to detect ectopic beats such as when a morphology of a primary ECG signal does not change due to the characteristics of the electrical activity. In order to use the additional signal from the secondary electrical sensor, changes in morphology and amplitude in different beats may be considered such that if a change is determined by the secondary electrical sensor, the beat(s) that are different are excluded from further analysis.

At 307, the method identifies mechanically inconsistent (MI) data within the motion data collection based on irregular changes in the motion data. For example, the identifying operation may analyze the motion data to identify changes in the motion data that exceed a predetermined threshold within a select period of time. The identifying operation may analyze the motion data to identify at least one of sudden or non-periodic changes in the motion data. The sudden and/or non-periodic changes are identified as MI data. The motion sensor 52 is located on the medical tool 16 that in general remains in contact with the region of interest. However, the medical tool 16 may become separated from the region of interest, in which case the motion sensor 52 will not move in the same manner as the heart wall. The identifying operation analyzes a waveform representative of the motion data over time to identify waveform characteristics indicative of separation between the medical tool and the region of interest. Inconsistent motion data or mechanical data is characterized by having an abrupt and non-periodic change of position in connection with at least two different position coordinates or channels due to the medical tool 16 being dislodged from the heart 14.

Additionally or alternatively, a change in amplitude and morphology of the motion data or mechanical data measured by the medical tool 16 may be used by the ECU 26 to determine whether the motion data from the motion sensor 52 is inconsistent. For example, the ECU 26 may calculate a reference waveform by averaging motion data waveforms measured by the medical tool 16 over a set number of cardiac cycles or amount of time. Once the reference waveform is calculated, the ECU 26 compares motion data against the reference waveform. If the ECU 26 determines the motion data has a deviation from the reference waveform by a predetermined amount, such as 2-3 mm, the motion data measured by the medical tool 16 is classified as inconsistent and is excluded from the associated cardiac cycle(s). Additionally or alternatively, the ECU 26 may calculate a correlation value based on the morphology of the motion data relative to the reference waveform. For example, if the correlation value is less than 0.8 the ECU 26 may determine that the motion data is inconsistent and is excluded from the associated cardiac cycle(s). If the correlation score is greater than or equal to 0.8, the ECU 26 may determine that the motion data is consistent and is included with the associated cardiac cycle(s). It should be noted that in other embodiments the predetermined base line may be greater than or less than 0.8.

Figure 5:
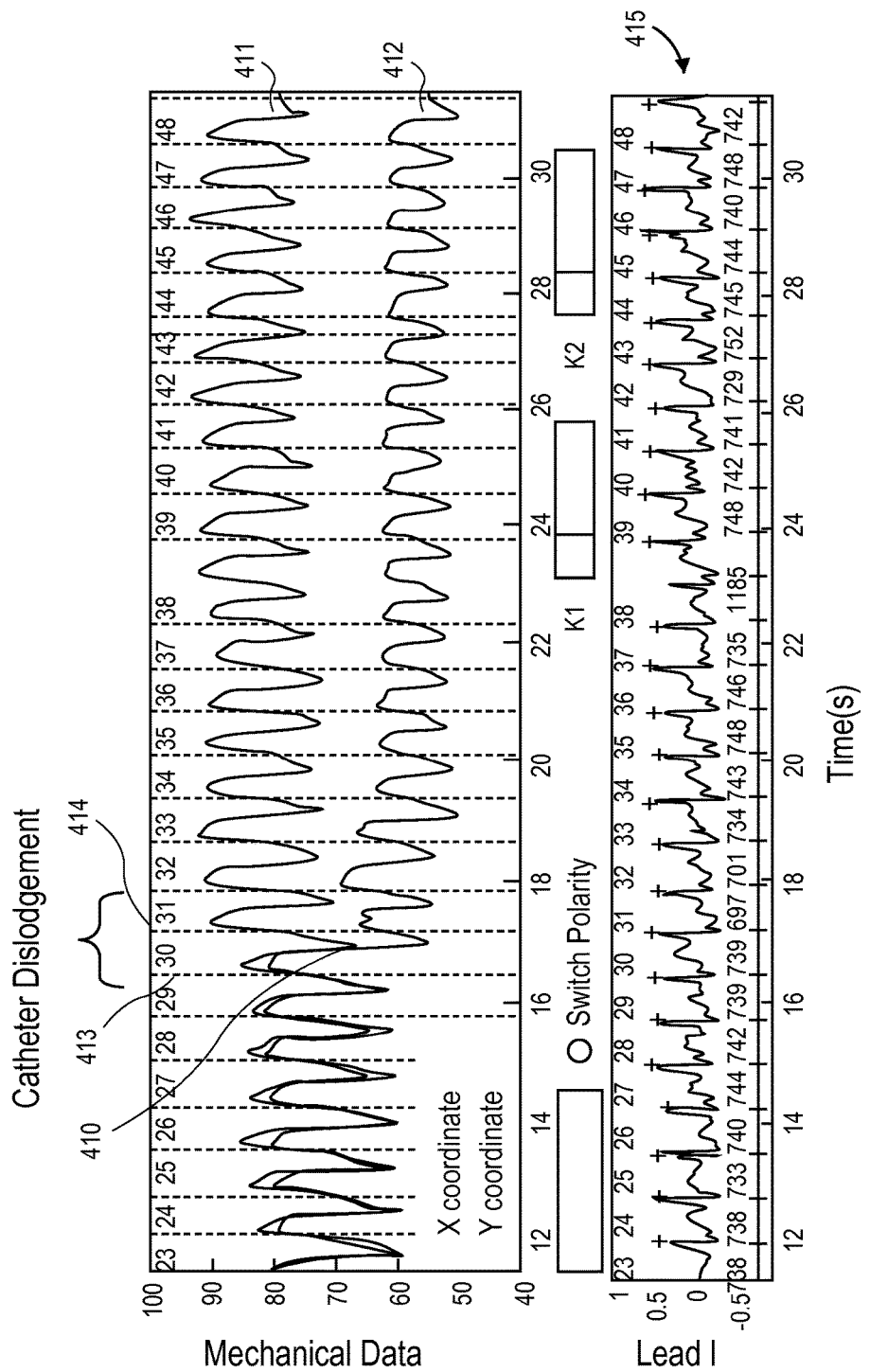
FIG. 5 illustrates motion data output from a motion sensor and electrical data output from an electric sensor as a function of time.

FIG. 5 illustrates motion waveforms 411 and 412 defined by motion data collected over multiple cardiac cycles by the motion data motion sensor 52. FIG. 5 further illustrates an electrical signal 415 collected over the cardiac cycles by ECG and/or IEGM sensors 53 and 55. The motion waveforms 411 and 412 correspond to movement along the x-coordinate and the y-coordinate, respectively. The ECU 26 may identify inconsistent mechanical data by comparing the current position 414 of the motion sensor (e.g., the motion sensor 52) at points along the motion waveforms 411 and 412 to a select preceding position coordinate 413 of the motion sensor 52. The ECU 26 may identify a shift in the position coordinates of the motion sensor 53 within a predetermined time frame that exceeds a predetermined position change threshold (e.g., 4 mm). When the shift exceeds the threshold, the motion data is classified or designated as inconsistent mechanical data for the associated cardiac cycle. As illustrated in FIG. 5, the ECU 26 may detect a simultaneous shift of the motion sensor position coordinate measurements at points in waveforms 411 and 412 at 410. In the example of FIG. 5, the two waveforms 411 and 412 shift by approximately 8 mm and 12 mm respectively, for one or more cardiac cycles which is greater than the predetermined position threshold of 4 mm. Thus, the ECU 26 may exclude the position or mechanical data from the motion data for the associated cardiac cycles after 410.

The motion data may be defined as the position of the motion sensor 52 of the medical tool 16 and/or the orientation of the motion sensor 52 relative to the C-arm support structure 28. The position measurement may be represented in a Cartesian coordinate (e.g., (X, Y, Z)) relative to a reference point of the navigation system 20. Additionally or alternatively, the position measurement may be a patient-specific cardiac coordinate system (e.g., Radial, circumferential, longitudinal) determined by the navigation system 20. Optionally, the motion data may be filtered or compensated by the ECU 26 to account for secondary sensor movements detected by the patient reference sensors 54 such as respiratory motion, patient or table movement relative to the medical tool 16, and movement of the c-arm support structure 28.

At 309, once the invalid or ectopic beats are identified, the ectopic beats and the corresponding motion data are removed from the motion data collection. At 309, the method removes at least a portion of the EI and MI data from the motion data collection based on the designating and identifying operations to form an electrically/mechanically consistent (EMC) motion data collection which is saved in the local storage medium 27. The removing operation removes the motion data associated with ectopic beats and removes motion data associated with at least a portion of neighboring beats that occur at least one of before or after the ectopic beats.

Figure 6:
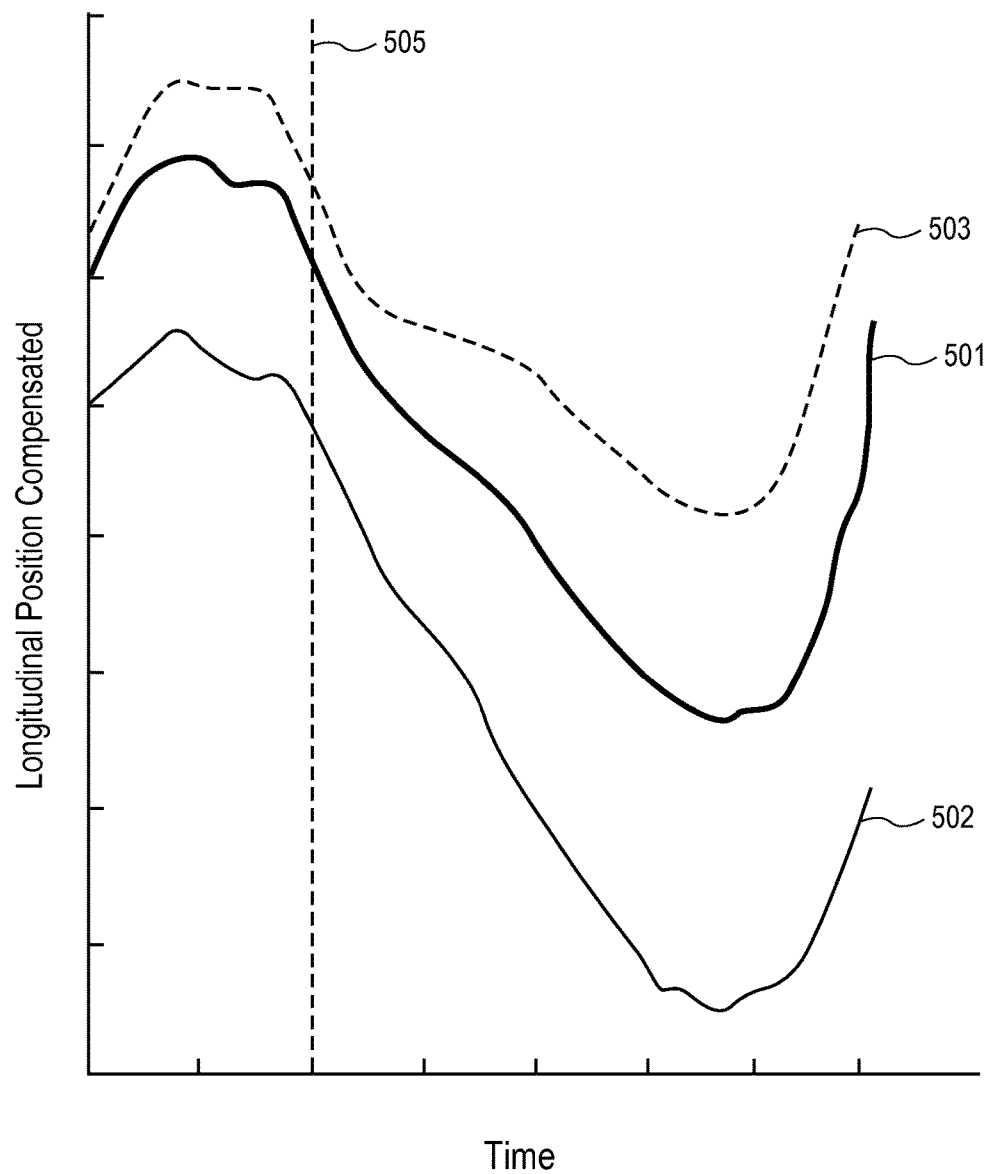
FIG. 6 illustrates motion characterization waveforms.

At 311, the method synchronizes the motion data and determines an average motion characterization waveform 501 for each map point. Once the mechanical inconsistencies and the ectopic beats are removed from the motion data, the remaining EMC motion data collection or selected beat waveforms (e.g., motion characterization waveforms 502, 503) are synchronized such that a feature(s) on the global ECG or IEGM waveform (e.g., each R-peak) are aligned by the ECU 26. FIG. 6 illustrates the motion characterization waveforms 502-503 aligned by the ECU 26. The average motion characterization waveform 501 is the average of the individual selected beat waveforms (e.g., motion characterization waveforms 502, 503) at each sample point. Selected beat waveforms (e.g., 502, 503) may be temporally equalized by stretching the waveforms that have shorter cycle lengths until the shorter beat waveforms have a length equal to the synchronization length or a predetermined interval for the cardiac cycle. An individual beat waveform may be "stretched" by performing interpolation upon the waveform of motion data to generate synthetic data values for points between the measured data values. Similarly, the selected beat waveforms, that have longer cycle lengths, may be temporally shortened or shrunk, such as through performing down sampling of the beat waveforms. Alternatively, the waveforms, defined by each map point, may be cut off at the end of the shortest cycle length.

The operations described above may represent real-time collection of motion data where dyssynchrony scores are supplied on a display to the physician while the tool continues to collect motion data. Alternatively, the motion data may have been previously collected and stored in memory, such as on a network server or hospital database. In this example, the operation at 301 simply accesses the network server or database to read the pre-existing motion data 250 (without real-time motion data collection).

Following the above operations, motion data 250 are now known for each map point of interest along the heart wall. The motion data for any PSMD collection (e.g., 220) may be represented as a corresponding motion waveform representative of movement during a single cardiac beat. For example, the horizontal axis may represent time from the beginning to end of a single heart beat. The vertical axis represents the amount of displacement or position change in the heart wall map point as measured from a start reference position.

It should be recognized that, in certain embodiments, the mapping tool may only collect data for a portion of the heart's endocardial or epicardial surface. For example, when performing epicardial mapping, the method may only collect data for map points along one or more veins that traverse the outside surface of the heart. Motion data may be limited to map points along the coronary sinus vein, its tributaries, the great cardiac vein, the middle cardiac vein and other veins along select anatomical regions.

Figure 7:
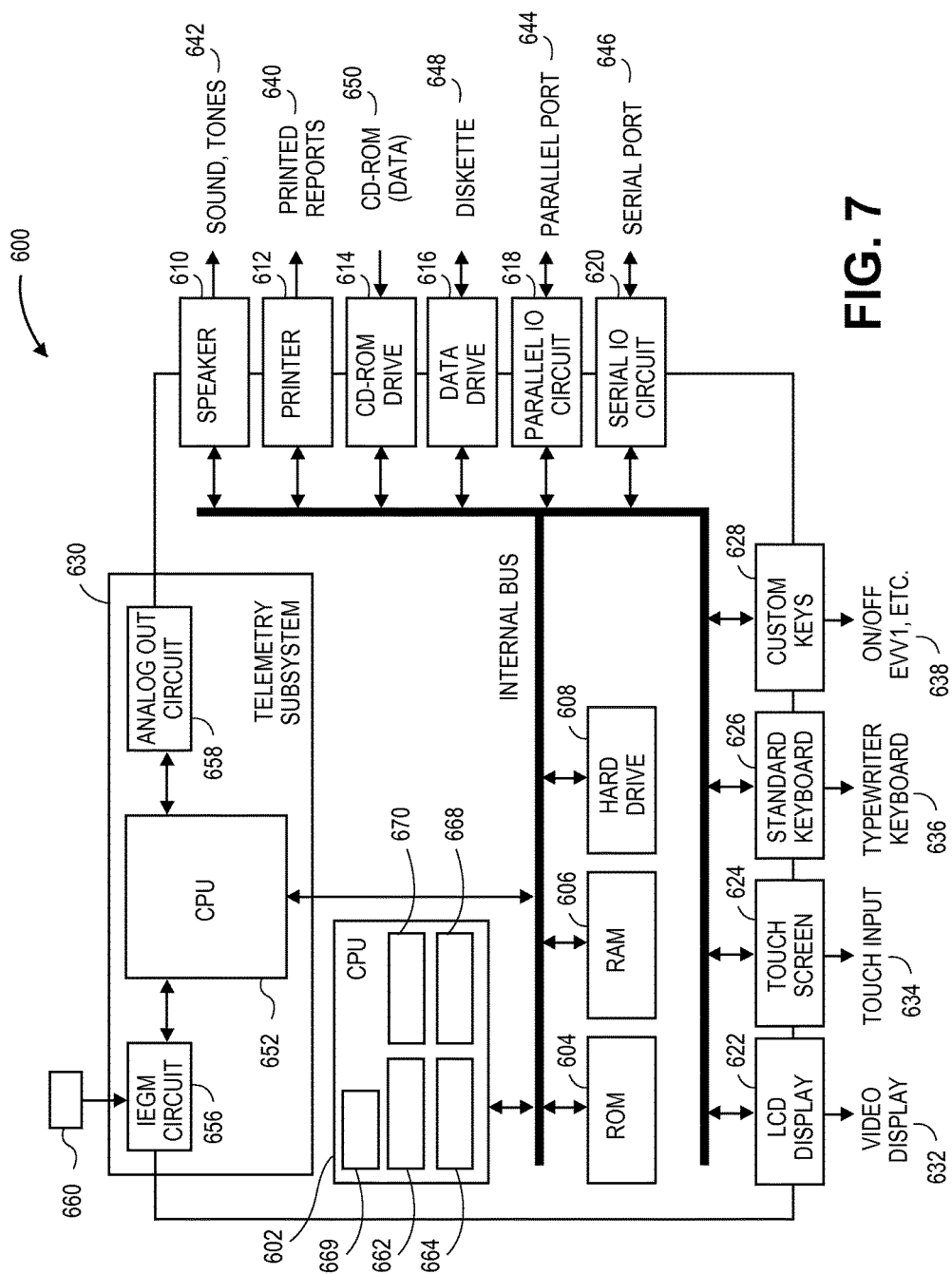
FIG. 7 illustrates a system for analyzing motion data in accordance with an embodiment.

FIG. 7 illustrates a functional block diagram of a navigation system 600 that is operated in accordance with the processes described herein to analyze motion and electrical data. The navigation system 600 may be a workstation, a portable computer, and the like. The navigation system 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and an electronic control unit (ECU) 630. The internal bus is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the navigation system 600. The CPU 602 performs the COI measurement process discussed above. The CPU 602 may include RAM or ROM memory, logic and timing circuitry, state machine circuitry, and I/O circuitry to interface with the IMD. The display 622 (e.g., the display 58) may be connected to the video display 632. The touch screen 624 may display graphic information relating to the IMD. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the ECU 630. Furthermore, custom keys 628 turn on/off 638 (e.g., EVVI) the navigation system 600. The printer 612 prints copies of reports and/or images 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The CPU 602 is configured to analyze motion data and electrical measurement data collected by the cardiovascular navigation system to identify electrical and motion data exhibited by a heart. The CPU 602 receives access to motion data (MD) sets, as explained herein. The CPU 602 includes an SSMD collection analysis circuit module 662 that divides the SSMD collections of data into quadrants associated with corresponding phases of the cardiac cycle with raw electrical and motion data.

The CPU 602 includes an electrical waveform analysis circuit module 664 that analyzes the electrical sensor measurements of the heart. The electrical waveform analysis circuit module 664 analyzes the electrical sensor measurements to locate ectopic beats within the electrical sensor measurement data. Once an ectopic beat is located, the analysis circuit module 664 removes the ectopic beat data from the motion data.

A position analysis circuit module 668 analyzes the position measurement of the heart based on at least two channels of the motion sensor. The position analysis circuit module 668 determines and locates inconsistent motion data based on the position measurements and removes the inconsistent data from the motion data.

The navigation system 600 includes one or more CPUs 602, and a local storage medium (e.g. ROM 604, RAM 606, HD 608) storing program instructions accessible by the CPU 602. Responsive to execution of the program instructions, the CPU 602 is configured to: designate ectopic beats within the cardiac cycles based on the electrical cardiac signals, the ectopic beats producing electrically inconsistent (EI) data within the motion data collection; identify mechanically inconsistent (MI) data within the motion data collection based on irregular changes in the motion data; and remove at least a portion of the EI and MI data from the motion data collection based on the designating and identifying operations to form an electrically/mechanically consistent (EMC) motion data collection. Optionally, the CPU 602 is configured to remove the EI motion data associated with ectopic beats and remove motion data associated with at least a portion of neighboring beats that occur at least one of before or after the ectopic beats. Optionally, the CPU 602 is configured to remove the MI data associated with the irregular changes and at least a portion of adjacent motion data that occurs at least one of before or after the irregular changes.

Additionally or alternatively, the CPU 602 is configured to analyze the motion data to identify changes in the motion data that exceed a predetermined threshold within a select period of time. Additionally or alternatively, the CPU 602 is configured to analyze the motion data to identify at least one of sudden or non-periodic changes in the motion data, the at least one of sudden or non-periodic changes being identified as MI data. The motion sensor is located on a medical tool in contact with the region of interest. Additionally or alternatively, the CPU 602 is configured to analyze a waveform representative of the motion data over time to identify waveform characteristics indicative of separation between the medical tool and the region of interest.

Additionally or alternatively, the CPU 602 is configured to analyze the motion data to calculate a correlation value based on a morphology of the motion data or mechanical data measured by the medical tool against a template motion data based on predetermined motion data stored on memory (e.g., ROM 604, RAM 606, HD 608) or calculated by the CPU 602 from averaging motion data over a plurality of cardiac cycles.

Additionally or alternatively, the CPU 602 is configured to repeat the acquiring, designating, identifying and removing operations for each of multiple map points on the region of interest to form separate EMC motion data collections for each of the multiple map points. Additionally or alternatively, the CPU 602 is configured to: perform the acquiring, designating, identifying and removing operations for a select map point; and determine a motion characterization waveform for the map point based on the EMC motion data collection and exclude the EI and MI data. The electrical cardiac signals define a cardiac waveform. Additionally or alternatively, the CPU 602 is configured to parse through the cardiac waveform to identify, as a characteristic representative of abnormal physiologic behavior, one or more of: i) when a peak amplitude of a QRS complex falls below a threshold amplitude; ii) when a QRS complex has a double-peaked or flat R-wave; iii) when consecutive R waves have an R-R interval that is longer than a select R-R interval by more than a cutoff value; iv) when a correlation score based on the morphology of the cardiac waveform is below a predetermined baseline. The motion data collection includes motion data associated with X, Y and Z coordinates of a reference coordinate system. Additionally or alternatively, the CPU 602 is configured to identify MI data based on irregular changes in the motion data along one or more of the X, Y and Z coordinates.

A dyssynchrony measure circuit module 669 calculates a measure of mechanical dyssynchrony associated with the map points of the wall based on at least one of i) whether the map points move in a select direction during select phases of the cardiac cycle; ii) whether the map points move by a select amount during the select phases; iii) a direction of strain waveform (increasing or decreasing) during select phases of the cardiac cycle, iv) an extent of strain during the select phases, and/or v) timing of shortening calculated based on strain measurements in different regions of the heart. Optionally, the calculation may calculate a proportion between total area and area portion that is moving in a select direction. In this example, when a select number of points are encompassed within a select area on the heart, the method calculates the proportion of the total surface area of the heart that this select area encompasses.

As one example, the measure circuit module 669 may determine, as the measure of dyssynchrony, a proportion of the map points (out of a global set of map points, out of all map points in a corresponding segment and the like) that are moving in the select direction. For example, the select direction may represent at least one of inward during a systole phase and outward during a diastole phase. As another example, the measure circuit module 669 may calculate, as the measure, a percentage of a number of map points that move in the select direction out of a total (global or within a common segment) number of map points. Optionally, the measure circuit module 669 may calculate a proportion between total area and area portion that is moving in a select direction. In this example, when a select number of points are encompassed within a select area on the heart, the method calculates the proportion of the total surface area of the heart that this select area encompasses.

The display 622 displays a dyssynchrony score based on the measure of dyssynchrony in connection with at least one of lead placement for a cardiac resynchronization therapy (CRT) device or programming optimization for a CRT device. The dyssynchrony score may be presented as a numeric value, a color according to a color coded score range, a graph, a word (e.g., high, medium, low) and the like.

The CPU 602 also includes a synchronization and averaging circuit module (SACM) 670. The SACM 670 receives the motion data from modules 664 and 668 and synchronizes the motion date for a corresponding map point. Once the motion data is synchronized, the SACM 670 calculates an average motion characterization waveform. The display 622 displays the average motion characterization waveform based on the calculations of the SACM 670.

The ECU 630 includes a central processing unit (CPU) 652, which communicates with both an IEGM circuit 656 and an analog out circuit 658. The circuit 656 may be connected to electrical sensors 660 to receive and process IEGM cardiac signals as discussed above.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method to identify motion data associated with consistent electrical and mechanical behavior for a region of interest of the heart, the method comprising:
    acquiring, via an electrical sensor, electrical cardiac signals indicative of physiologic behavior of at least a portion of the heart over a plurality of cardiac cycles;
    acquiring, via a motion sensor, motion data indicative of mechanical behavior of a motion sensor over the plurality of cardiac cycles to form a motion data collection, the motion data indicative of mechanical behavior of the region of interest when the motion sensor is in contact with the region of interest;
    designating, via a processor, ectopic beats or arrhythmias within the cardiac cycles based on the electrical cardiac signals, the ectopic beats producing electrically inconsistent (EI) data within the motion data collection;
    identifying, via the processor, mechanically inconsistent (MI) data within the motion data collection based on irregular changes in the motion data; and
    removing, via the processor, at least a portion of the EI and MI data from the motion data collection based on the designating and identifying operations to form an electrically/mechanically consistent (EMC) motion data collection.

2. The method of claim 1, wherein the removing operation removes the EI data associated with ectopic beats and removes motion data associated with at least a portion of neighboring beats that occur at least one of before or after the ectopic beats.

3. The method of claim 1, wherein the removing operation removes the MI data associated with the irregular changes and at least a portion of adjacent motion data that occurs at least one of before or after the irregular changes.

4. The method of claim 1, wherein the identifying operation analyzes the motion data to identify changes in the motion data that exceed a predetermined threshold within a select period of time.

5. The method of claim 1, wherein the identifying operation analyzes the motion data to identify at least one of sudden or non-periodic changes in the motion data, the at least one of sudden or non-periodic changes being identified as MI data.

6. The method of claim 1, wherein the motion sensor is located on a medical tool in contact with the region of interest, the identifying operation analyzes a waveform representative of the motion data over time to identify waveform characteristics indicative of separation between the medical tool and the region of interest.

7. The method of claim 1, further comprising repeating the acquiring, designating, identifying and removing operations for each of multiple map points on the region of interest to form separate EMC motion data collections for each of the multiple map points.

8. The method of claim 1, wherein the acquiring, designating, identifying and removing operations are performed for a select map point, the method further comprising determining a motion characterization waveform for the map point based on the EMC motion data collection and excluding the EI and MI data.

9. The method of claim 1, wherein the electrical cardiac signals define a cardiac waveform, the designating operation includes parsing through the cardiac waveform to identify, as a characteristic representative of abnormal physiologic behavior, one or more of:
   i) when a peak amplitude of a QRS complex falls below a threshold amplitude;
   ii) when a QRS complex has a double-peaked or flat R-wave;
   iii) when consecutive R waves have an R-R interval that is longer than a select R-R interval by more than a cutoff value; and
   iv) when a correlation score based on the morphology of the cardiac waveform is below a predetermined baseline.

10. The method of claim 1, wherein the motion data collection includes motion data associated with X, Y and Z coordinates of a reference coordinate system, the identifying operation identifying MI data based on irregular changes in the motion data along one or more of the X and Y coordinates.

11. A system to identify motion data associated with consistent electrical and mechanical behavior for a region of interest of the heart, the system comprising:
   a processor;
   an electrical sensor configured to acquire electrical cardiac signals indicative of physiologic behavior of at least a portion of the heart over a plurality of cardiac cycles;
   a motion sensor on a medical tool, the motion sensor configured to acquire motion data indicative of mechanical behavior of the motion sensor over the plurality of cardiac cycles to form a motion data collection, the motion data indicative of mechanical behavior of the region of interest when the motion sensor is in contact with the region of interest;
   a local storage medium storing program instructions accessible by the processor;
   wherein, responsive to execution of the program instructions, the processor is configured to:
      designate ectopic beats within the cardiac cycles based on the electrical cardiac signals, the ectopic beats producing electrically inconsistent (EI) data within the motion data collection;
      identify mechanically inconsistent (MI) data within the motion data collection based on irregular changes in the motion data; and
      remove at least a portion of the EI and MI data from the motion data collection based on the designating and identifying operations to form an electrically/mechanically consistent (EMC) motion data collection.

12. The system of claim 11, wherein the processor is configured to remove the EI data associated with ectopic beats and remove motion data associated with at least a portion of neighboring beats that occur at least one of before or after the ectopic beats.

13. The system of claim 11, wherein the processor is configured to remove the MI data associated with the irregular changes and at least a portion of adjacent motion data that occurs at least one of before or after the irregular changes.

14. The system of claim 11, wherein the processor is configured to analyze the motion data to identify changes in the motion data that exceed a predetermined threshold within a select period of time.

15. The system of claim 11, wherein the processor is configured to analyze the motion data to identify at least one of sudden or non-periodic changes in the motion data, the at least one of sudden or non-periodic changes being identified as MI data.

16. The system of claim 11, wherein the motion sensor is located on a medical tool in contact with the region of interest and wherein the processor is configured to analyze a waveform representative of the motion data over time to identify waveform characteristics indicative of separation between the medical tool and the region of interest.

17. The system of claim 11, wherein the processor is configured to repeat the acquiring, designating, identifying and removing operations for each of multiple map points on the region of interest to form separate EMC motion data collections for each of the multiple map points.

18. The system of claim 11, wherein the processor is configured to: perform the acquiring, designating, identifying and removing operations for a select map point; and determine a motion characterization waveform for the map point based on the EMC motion data collection and exclude the EI and MI data.

19. The system of claim 11, wherein the electrical cardiac signals define a cardiac waveform, and wherein the processor is configured to parse through the cardiac waveform to identify, as a characteristic representative of abnormal physiologic behavior, one or more of:
   i) when a peak amplitude of a QRS complex falls below a threshold amplitude;
   ii) when a QRS complex has a double-peaked or flat R-wave;
   iii) when consecutive R waves have an R-R interval that is longer than a select R-R interval by more than a cutoff value; and iv) when a correlation score based on the morphology of the cardiac waveform is below a predetermined baseline.

20. The system of claim 11, wherein the motion data collection includes motion data associated with X, Y and Z coordinates of a reference coordinate system, the processor is configured to identify MI data based on irregular changes in the motion data along one or more of the X, Y and Z coordinates.

* * * * *